(12) United States Patent
Shen et al.

(10) Patent No.: US 10,758,113 B2
(45) Date of Patent: Sep. 1, 2020

(54) MEDICAL OTOSCOPE

(71) Applicant: ZUMAX MEDICAL CO., LTD., Suzhou, Jiangsu (CN)

(72) Inventors: Shunguo Shen, Jiangsu (CN); Jianyue Li, Jiangsu (CN); Jilong Wang, Jiangsu (CN)

(73) Assignee: Zumax Medical Co., Ltd, Suzhou (CN)

( * ) Notice: Subject to any disclaimer, the term of this patent is extended or adjusted under 35 U.S.C. 154(b) by 0 days.

(21) Appl. No.: 16/082,958

(22) PCT Filed: Dec. 27, 2016

(86) PCT No.: PCT/CN2016/112394
§ 371 (c)(1),
(2) Date: Sep. 7, 2018

(87) PCT Pub. No.: WO2017/152701
PCT Pub. Date: Sep. 14, 2017

(65) Prior Publication Data
US 2019/0082946 A1 Mar. 21, 2019

(30) Foreign Application Priority Data
Mar. 8, 2016 (CN) .......................... 2016 1 0130212

(51) Int. Cl.
*A61B 1/227* (2006.01)
*A61B 1/00* (2006.01)
*A61B 1/06* (2006.01)

(52) U.S. Cl.
CPC ............ *A61B 1/227* (2013.01); *A61B 1/0019* (2013.01); *A61B 1/00163* (2013.01); *A61B 1/00188* (2013.01); *A61B 1/06* (2013.01)

(58) Field of Classification Search
CPC ............ A61B 1/00163; A61B 1/00188; A61B 1/0019; A61B 1/227; A61B 1/233; A61B 1/24; A61B 1/273
See application file for complete search history.

(56) References Cited

U.S. PATENT DOCUMENTS 3,384,076 A * 5/1968 Speelman ............... A61B 1/227
600/200
3,874,371 A * 4/1975 Stader .................... A61B 1/227
600/200

(Continued)

FOREIGN PATENT DOCUMENTS

AU 2004261180 A1 2/2005
AU 2004264876 A1 2/2005

(Continued)

OTHER PUBLICATIONS

International Search Report for Application No. PCT/CN2016/112394, dated Mar. 31, 2017.

(Continued)

*Primary Examiner* — Larry E Waggle, Jr.
(74) *Attorney, Agent, or Firm* — Kramer Levin Naftalis & Frankel, LLP

(57) ABSTRACT

A medical otoscope, comprises an otoscope body and an observation apparatus connected to one end of the otoscope body, the other end of the otoscope body having a tapered portion capable of inserting into an ear, the observation apparatus comprising at least one optical lens group arranged along a same optical axis, the optical lens group comprising at least one optical lens capable of moving along the optical axis, central axis of the observation apparatus being coaxial with or deviating from central axis of the otoscope body. The focal length of the medical otoscope can be adjusted by means of arranging two groups of optical (Continued)

lenses movable relative to one another, and the medical otoscope has a simple structure and is convenient for operation.

7 Claims, 2 Drawing Sheets

(56) References Cited

U.S. PATENT DOCUMENTS

| | | | |
|---|---|---|---|
| 4,006,738 A | | 2/1977 | Moore et al. |
| 7,354,399 B2 * | | 4/2008 | Strom .................... A61B 1/227 600/200 |
| 7,399,275 B2 | | 7/2008 | Goldfain et al. |
| 7,803,110 B2 | | 9/2010 | Goldfain et al. |
| 8,066,634 B2 | | 11/2011 | Andreassen et al. |
| 8,136,986 B2 | | 3/2012 | Lane et al. |
| 8,197,403 B2 | | 6/2012 | Strom et al. |
| 8,469,882 B2 | | 6/2013 | Andreassen et al. |
| 2005/0027168 A1 | | 2/2005 | Strom et al. |
| 2005/0027169 A1 | | 2/2005 | Goldfain et al. |
| 2006/0252996 A1 | | 11/2006 | Goldfain et al. |
| 2008/0051637 A1 | | 2/2008 | Andreassen et al. |
| 2008/0123717 A1 | | 5/2008 | Lane et al. |
| 2008/0139888 A1 | | 6/2008 | Strom et al. |
| 2012/0065473 A1 | | 3/2012 | Andreassen et al. |
| 2013/0083183 A1 | | 4/2013 | Cheng et al. |
| 2013/0267784 A1 | | 10/2013 | Andreassen et al. |
| 2014/0336467 A1 | | 11/2014 | Eder et al. |
| 2015/0223669 A1 | | 8/2015 | Goldfain |
| 2016/0143518 A1 | | 5/2016 | Harris |

FOREIGN PATENT DOCUMENTS

| | | |
|---|---|---|
| AU | 2004261180 B2 | 9/2009 |
| AU | 2004264876 B2 | 4/2010 |
| BR | 7507925 A | 2/1977 |
| CA | 1047292 A | 1/1979 |
| CA | 2533826 A1 | 2/2005 |
| CA | 2534762 A1 | 2/2005 |
| CA | 2533826 C | 6/2012 |
| CN | 1829468 A | 9/2006 |
| CN | 1829468 A | 9/2006 |
| CN | 1984599 A | 6/2007 |
| CN | 201602744 U | 10/2010 |
| CN | 1984599 B | 11/2010 |
| CN | 1829468 B | 7/2012 |
| CN | 102894950 A | 1/2013 |
| CN | 103027664 A | 4/2013 |
| CN | 104800000 A | 7/2015 |
| CN | 103027664 B | 5/2016 |
| DE | 102013208382 A1 | 11/2014 |
| DK | 445775 A | 12/1976 |
| DK | 7504457 A | 1/1977 |
| EP | 1659923 A2 | 5/2006 |
| EP | 1659927 A1 | 5/2006 |
| EP | 2368932 A1 | 9/2011 |
| EP | 2578140 A1 | 4/2013 |
| EP | 2368932 B1 | 1/2014 |
| EP | 1659927 B1 | 5/2015 |
| EP | 1659923 B1 | 2/2016 |
| EP | 2578140 B1 | 4/2016 |
| FR | 2313006 A1 | 12/1976 |
| FR | 2313006 B3 | 8/1978 |
| GB | 1498474 A | 1/1976 |
| IL | 173280 A | 4/2010 |
| IL | 173279 A | 11/2010 |
| JP | S51148286 A | 12/1976 |
| JP | S5330958 B2 | 8/1978 |
| JP | 2007500541 A | 1/2007 |
| JP | 2007500542 A | 1/2007 |
| NZ | 544954 A | 7/2008 |
| NZ | 544953 A | 12/2008 |
| SE | 7512655 A | 12/1976 |
| TW | 201225896 A | 7/2012 |
| TW | I432167 B | 4/2014 |
| WO | 2005011484 A1 | 2/2005 |
| WO | 2005016117 A2 | 2/2005 |
| WO | 2005016117 A9 | 2/2005 |

OTHER PUBLICATIONS

PCT Written Opinion for Appl. No. PCT/CN2016/112394, dated Mar. 31, 2017.
Notification of the First Office Action for Appl. No. CN 201610130212.0, dated Jun. 28, 2018.
Notification of the Second Office Action for Appl. No. CN 201610130212.0, dated Mar. 25, 2020.
Rejection of Decisions for Appl. No. CN 201610130212.0, dated Jul. 2, 2019.

* cited by examiner

MEDICAL OTOSCOPE

TECHNICAL FIELD OF THE INVENTION

The present disclosure relates to the medical diagnostic instrument field, in particular to a medical otoscope.

BACKGROUND OF THE INVENTION

Otoscopes are hand-held instruments that are well-known in the medical diagnostic instrument field for professionals and health care providers to examine the patient's ears.

The traditional otoscope includes an otoscope body and an observation apparatus connected to one end of the otoscope body, the other end of the otoscope body has a tapered portion, and the observation apparatus is generally provided with an optical glass such as a lens. When in use, the tapered portion is sheathed by an ear speculum, the ear speculum is inserted into an ear for a certain distance, and the ear is inspected through the observation device.

However, the focal length of the traditional otoscope is fixed, and the distance within the ear is limited. The traditional otoscopes also have optical lenses within the otoscope body to shorten the focal length and increase the viewing distance, but there is also the problem of limited observation. Referring to the otoscope described in Chinese Patent Publication CN1829468A, it discloses an otoscope including an observation apparatus, an imaging lens array, and a focusing mechanism, the observation range is enlarged through imaging via the imaging lens array, and meanwhile the focal length is adjusted by the relative movement of the imaging lens array and the observation apparatus, however, the structure thereof is complex and it is also inconvenient to operate.

SUMMARY OF THE INVENTION

The purpose of the present disclosure is to provide a medical otoscope with a simple structure and an adjustable focal length.

To achieve the above purpose, the technical solution employed by the present disclosure is:

A medical otoscope comprises an otoscope body and an observation apparatus connected to one end of the otoscope, wherein the other end of the otoscope body has a tapered portion for inserting into an ear, the observation apparatus comprises at least one optical lens group arranged along a same optical axis, the optical lens group comprises at least one optical lens capable of moving along the optical axis, and central axis of the observation apparatus is coaxial with or deviates from a central axis of the otoscope body.

Preferably, the optical lens group comprises a first optical lens and a second optical lens arranged along a same optical axis, and the first optical lens and the second optical lens are capable of moving along the optical axis relative to each other.

Further preferably, when the central axis of the observation apparatus is capable of being coaxial with or deviate from the central axis of the otoscope body, the observation apparatus is rotatably connected to the otoscope body via a rotating shaft, and axis of the rotating shaft extends in the same direction as the central axis of the otoscope body.

Further preferably, the observation apparatus further comprises a connecting housing connected to the otoscope body, and the first optical lens is fixedly provided within the connecting housing.

Further preferably, the observation apparatus further comprises an adjusting housing connected to the connecting housing, the second optical lens is provided within the adjusting housing, and the second optical lens moves with respect to the first optical lens along the optical axis when operating the adjusting housing.

Further preferably, the adjusting housing is rotatably connected to the connecting housing, and the second optical lens moves with respect to the first optical lens along the optical axis when rotating the adjusting housing.

Further preferably, the first optical lens comprises a positive lens; the second optical lens comprises a negative lens.

Preferably, the otoscope body has a hollow inner cavity communicated with the tapered portion, and the inner cavity is provided with an illuminating apparatus therein.

Preferably, an ear speculum is detachably mounted on the tapered portion.

Due to the use of the above technical solutions, the present invention has the following advantages over the prior art:

In the present disclosure, the focal length of the otoscope can be adjusted by means of arranging two groups of optical lenses movable relative to one another, and the otoscope has a simple structure and is convenient for operation.

DETAILED DESCRIPTION OF EXEMPLARY EMBODIMENTS

Figure 1:
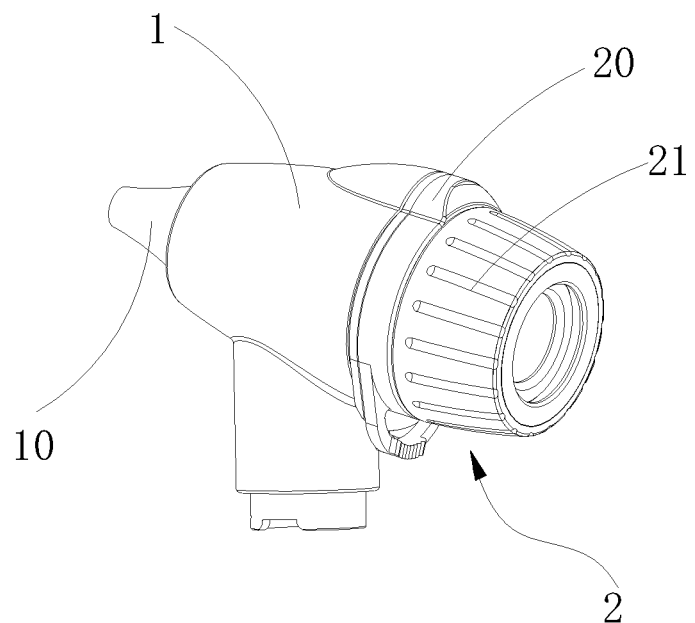
FIG. 1 is a stereograms of the embodiment.

In the following, the present disclosure are described in detail combining with the accompanying drawings and embodiments.

A medical otoscope as shown in the figures, comprises an otoscope body 1 and an observation apparatus 2 connected to one end of the otoscope 1, the other end of the otoscope body 1 has a tapered part 10 for inserting into an ear, the otoscope body 1 has a hollow inner cavity 11 communicated with the tapered portion 10, and an ear speculum 3 is detachably mounted on the tapered portion 10.

Figure 2:
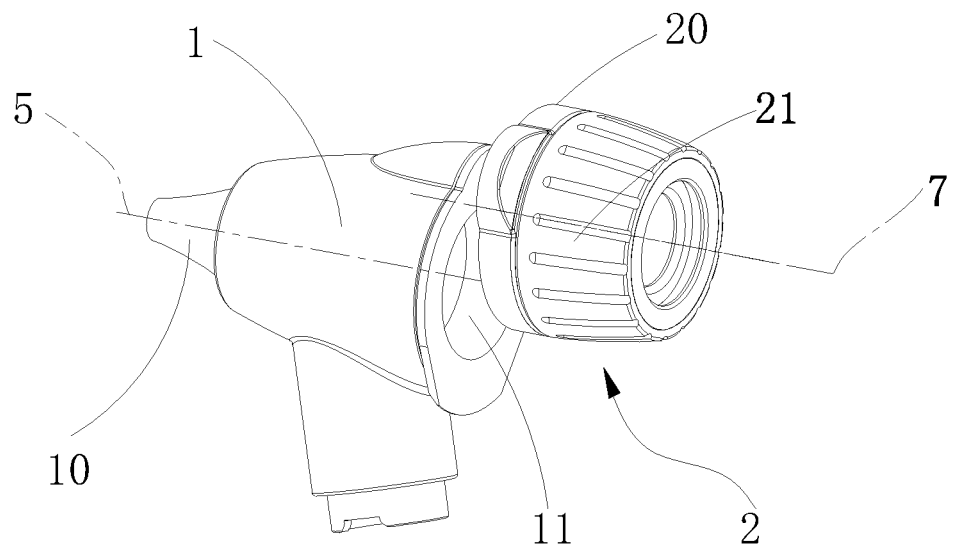
FIG. 2 is a use state diagram of the embodiment.

In the embodiment, the observation apparatus 2 comprises a connecting housing 20 connected to the otoscope body 1 and an adjusting housing 21 connected to the connecting housing 20. When the connecting housing 20 is fixed with respect to the otoscope body 1, the central axis 7 of the observation apparatus 2 can only coaxial with the central axis 5 of the otoscope body 1; when the connecting housing 20 is rotatably connected to the otoscope body 1 via a rotating shaft 8 and the axis 6 of the rotating shaft 8 extends in the same direction as the central axis 5 of the otoscope body 1, rotating the connecting housing 20 may cause the central axis 7 of the entire observation apparatus 2 and the central axis 5 of the otoscope body 1 to be adjusted between being coaxial with or deviating from each other, as shown in FIGS. 1 and 2.

Figure 3:
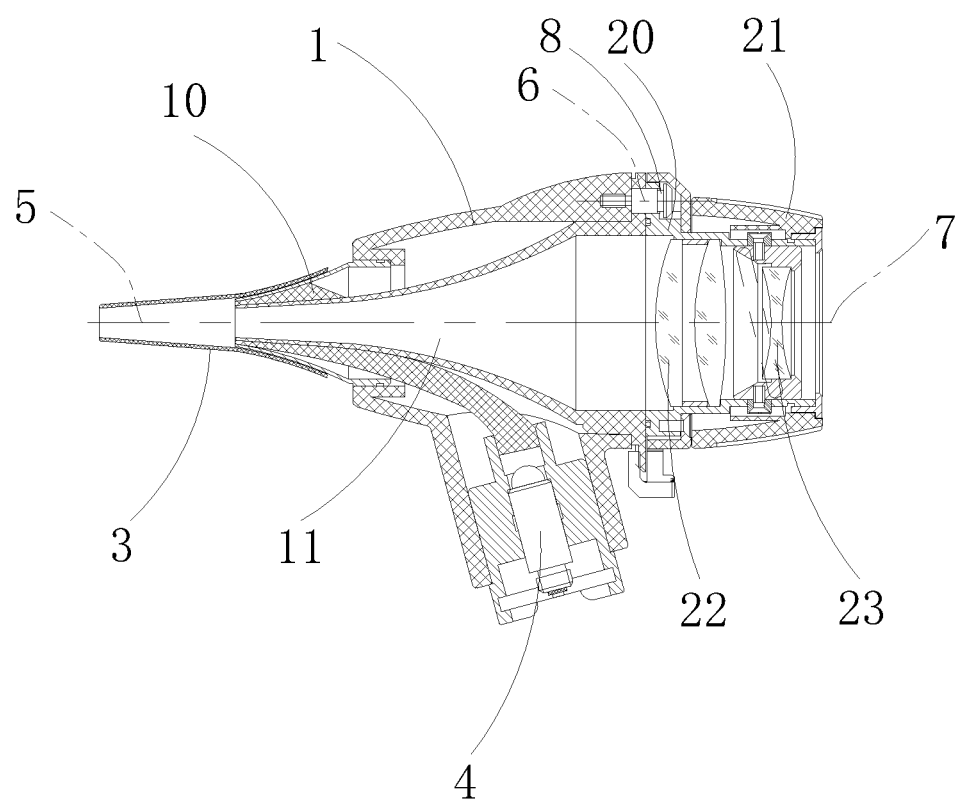
FIG. 3 is a schematic sectional view of the embodiment;
wherein, 1—otoscope body; 10—tapered portion; 11—inner cavity; 2—observation apparatus; 20—connecting housing; 21—adjusting housing; 22—first optical lens; 23—second optical lens; 3—ear speculum; 4—illuminating apparatus.

As shown in FIG. 3, the observation apparatus 2 further comprises a first optical lenses 22 and a second optical lens 23 arranged along a same optical axis, wherein, the first optical lenses 22 are consisted of two positive lenses fixedly provided within the connection housing 20, and the second optical lens 23 is a negative lens provided within the adjusting housing 21. In the embodiment, the adjusting housing 21 is rotatably connected to the connecting housing 20, the specific structure may be a thread structure or other conventional adjusting structure, that is, the adjusting housing 21 may be considered to be a rotary knob, and the second optical lens 23 moves with respect to the first optical lens 22 along the optical axis when rotating the adjusting housing 21. This allows the focal length of the optical lens group to be adjusted to achieve the adjustment within the visual field range.

In addition, an illuminating apparatus 4 is provided within the inner cavity 11. When in use, also may rotate the connecting housing 20, such that the central axis 7 of the entire observation apparatus 2 deviates from the central axis 5 of the otoscope body 1, the hollow inner cavity 11 of the otoscope body 1 exposes, and an examination component may also be extended into the ear via the inner cavity 11 for operation during observation via the observation apparatus 2.

The embodiments described above are only for illustrating the technical concepts and features of the present disclosure, and are intended to make those skilled in the art being able to understand the present disclosure and thereby implement it, and should not be concluded to limit the protective scope of this disclosure.

What is claimed is:

1. A medical otoscope, comprising an otoscope body and an observation apparatus connected to one end of the otoscope body, wherein the other end of the otoscope body has a tapered portion capable of inserting into an ear, the observation apparatus comprises at least one optical lens group arranged along a same optical axis, the optical lens group comprises a first optical lens and a second optical lens arranged along the same optical axis, and the first optical lens and the second optical lens are capable of moving along the optical axis relative to each other, the observation apparatus is rotatably connected to the otoscope body via a rotating shaft, and an axis of the rotating shaft extends in the same direction as a central axis of the otoscope body, the medical otoscope has two states, when in a first state, a central axis of the observation apparatus is coaxial with the central axis of the otoscope body; when in a second state, the central axis of the observation apparatus is parallel to the central axis of the otoscope body.

2. The medical otoscope according to claim 1, wherein the observation apparatus further comprises a connecting housing connected to the otoscope body, and the first optical lens is fixedly provided within the connecting housing.

3. The medical otoscope according to claim 2, wherein the observation apparatus further comprises an adjusting housing connected to the connection housing, the second optical lens is provided within the adjustment housing, and the second optical lens moves with respect to the first optical lens along the optical axis when operating the adjusting housing.

4. The medical otoscope according to claim 3, wherein the adjusting housing is rotatably connected to the first optical lens, and the second optical lens moves with respect to the first optical lens along the optical axis when rotating the adjusting housing.

5. The medical otoscope according to claim 1, wherein the first optical lens comprises a positive lens; and the second optical lens comprises a negative lens.

6. The medical otoscope according to claim 1, wherein the otoscope body has a hollow inner cavity communicating with the tapered portion, and an illuminating apparatus is provided within the inner cavity.

7. The medical otoscope according to claim 1, wherein an ear speculum is detachably mounted on the tapered portion.

\* \* \* \* \*